United States Patent [19]

Fahmy

[11] 4,268,508

[45] May 19, 1981

[54] O-ALKYL-S-BRANCHED ALKYL-ALKYLPHOSPHONODITHIOATE

[75] Inventor: Mohamed A. Fahmy, Edison, N.J.

[73] Assignee: Mobil Oil Corporation, Fairfax, Va.

[21] Appl. No.: 107,819

[22] Filed: Dec. 28, 1979

[51] Int. Cl.³ .......................... A01N 57/20; C07F 9/40
[52] U.S. Cl. ...................................... 424/222; 260/961
[58] Field of Search ......................... 260/961; 424/222

[56] References Cited

U.S. PATENT DOCUMENTS

| | | | |
|---|---|---|---|
| 3,121,662 | 2/1964 | Schrader | 260/961 |
| 3,209,020 | 9/1965 | Schrader | 260/961 |
| 3,642,960 | 2/1972 | Pitt et al. | 260/961 |
| 3,751,530 | 8/1973 | Oswald et al. | 260/961 |

Primary Examiner—Anton H. Sutto
Attorney, Agent, or Firm—C. A. Huggett; M. G. Gilman; E. J. Trojnar

[57] ABSTRACT

Compounds having the formula

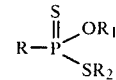

in which R and $R_1$ are alkyl of 1 to 8 carbon atoms, and $R_2$ is branched alkyl of 3 to 8 carbon atoms, and their use as insecticides and nematocides, e.g., in controlling corn rootworm, are disclosed.

26 Claims, No Drawings

O-ALKYL-S-BRANCHED ALKYL-ALKYLPHOSPHONODITHIOATE

CROSS-REFERENCE TO RELATED APPLICATIONS

An application entitled "BRANCHED-S-ALKYL PHOSPHONODITHIOIC HALIDE INTERMEDIATES AND PROCESS FOR THEIR PRODUCTION", Ser. No. 071,465, filed on Aug. 31, 1979 in the name of Mohamed A. Fahmy discloses certain intermediates useful for the production of insecticides and nematocides of this invention and the process for their preparation. An application entitled "UNSYMMETRICAL THIOPHOSPHONATE INSECTICIDES AND NEMATOCIDES", Ser. No. 071,464, filed Aug. 31, 1979 in the name of Jerry G. Strong discloses certain S-alkyl-S-branched alkyl-alkylphosphonotrithioates.

SUMMARY OF THE INVENTION

This invention relates to O-alkyl-S-branched alkyl-alkylphosphonodithioate compounds and their use as insecticides and nematocides.

More particularly, the compounds of the invention have the formula

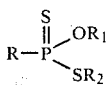

in which R is alkyl of 1 to 8 carbon atoms; $R_1$ is alkyl of 1 to 8 carbon atoms; and $R_2$ is branched alkyl of 3 to 8 carbon atoms.

These compounds exhibit a wide range of insecticidal activity and are of particular interest in controlling corn rootworm because of their excellent activity against this pest and their low phytotoxicity to corn plants.

DETAILED DESCRIPTION OF THE INVENTION

An important structural feature of the compounds of this invention is that $R_2$ in the above formula is branched alkyl. Certain alkylphosphonodithioate insecticides are described in U.S. Pat. No. 3,209,020. However, none of the species described in the patent correspond to the above formula where $R_2$ is branched alkyl.

It has been found that the branched compounds of this invention possess unexpected advantageous properties. In particular, they exhibit low phytotoxicity to corn. Since the activity of the branched compounds against corn rootworm is good and their phytotoxicity to corn is low the compounds of this invention are of special interest for controlling corn rootworm.

The compounds disclosed herein can be prepared by the method described in U.S. Pat. No. 3,209,020. Preferably, the compounds of this invention are prepared from a starting material which is a S-alkyl alkylphosphonodithioic halide, the preparation of which is illustrated in Example 1. A more detailed description of the preparation of these starting materials is contained in an application by M. Fahmy, Ser. No. 071,465, filed on Aug. 31, 1979, which application is incorporated herein by reference. The S-alkyl alkylphosphonodithioic halide is reacted with an alcohol in the presence of a base to arrive at the compounds of this invention.

The preferred reaction scheme is as follows:

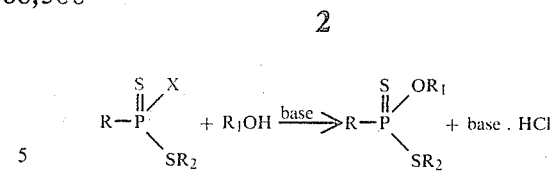

in which
R is alkyl of 1 to 8 carbon atoms;
$R_1$ is alkyl of 1 to 8 carbon atoms;
$R_2$ is branched alkyl of 3 to 8 carbon atoms; and
X is halogen, preferably Cl.

The reaction is advantageously carried out at a temperature of about 0° C. to 100° C. in an organic solvent in the presence of a tertiary amine, water or aqueous base, such as aqueous NaOH, or by producing the alkali salt of the alcohol using alkali metals such as sodium.

Suitable organic solvents are, for example, benzene, toluene, cyclohexane and 2-butanone, or the alcohol itself.

Suitable tertiary amines include trimethylamine, triethylamine, dimethylaniline, diethylaniline and pyridine.

The alkylphosphonodithioate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well-known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 lbs/acre. Under ideal conditions, depending on the pest to be controlled, the lower rate may offer adequate protections. On the other hand, adverse weather conditions, resistence of the pest and other factors may require that the active ingredient be used in higher proportions.

When the pest is soil-borne, the formulation containing the active ingredient is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting, after planting but before sprouting has taken place or after sprouting.

The following Examples illustrate the preparation of the compounds of this invention and their pesticidal properties. It will be understood that all of the compounds disclosed herein can be prepared by methods analogous to those described below.

EXAMPLE 1

Preparation of S-tert.-butyl ethylphosphonodithioic chloride (Intermediate)

To a solution of ethylphosphonothioic dichloride (80 g, 0.5 mol) in 500 ml dry toluene, was added 2:methyl-2-propanethiol (50 g, 0.55 mol). The solution was stirred while triethylamine (60 g, 0.6 mol) was added dropwise. After the complete addition of the amine, the mixture was stirred and heated up to 80° C. for three hours and allowed to stand overnight. The reaction mixture was washed with 5% cold HCl solution (100 ml), followed by another wash with 5% cold NaOH solution (100 ml), finally washed twice with water (100 ml each), and dried over magnesium sulfate. Toluene was evaporated under a water aspirator vacuum, and the oil residue was distilled. The product distilled at 78°–80° C./0.2 mm. The yield was 60 g (55.4% of theoretical yield). The structure was confirmed by NMR.

EXAMPLE 2

Preparation of O-ethyl-S-tert.-butyl-ethylphosphonodithioate

Sodium (1.0 g, 0.043 g/atom) was dissolved in 50 ml anhydrous ethanol. To this solution was added S-tert.-butyl-ethylphosphonodithioic chloride (8.0 g, 0.037 mol) in one portion. The mixture was stirred at room temperature for two hours. The reaction mixture was concentrated under vacuum, and the residual liquid was taken up in ether. The ether solution was washed with water, and dried over anhydrous Na$_2$SO$_4$. Ether was stripped off under vacuum, and the residual liquid was distilled, to give 6.5 g of product; b.p. 71–72/0.1 mm (77.7% yield). The structure was confirmed by NMR.

EXAMPLES 3–12

In a manner analogous to that of Example 2 the following compounds were prepared.

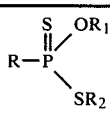

| Example | R | R$_1$ | R$_2$ | B.p.°C./mm | % yield |
|---|---|---|---|---|---|
| 3 | C$_2$H$_5$ | CH$_3$ | tert.-butyl | 66–68/0.1 | 76 |
| 4 | CH$_3$ | CH$_3$ | tert.-butyl | 50–52/0.3 | 86 |
| 5 | CH$_3$ | C$_2$H$_5$ | tert.-butyl | 60–62/0.1 | 75.3 |
| 6 | CH$_3$ | C$_3$H$_7$ | tert.-butyl | 74–75/0.07 | 75.3 |
| 7 | C$_2$H$_5$ | C$_3$H$_7$ | tert.-butyl | 84–85/0.07 | 72 |
| 8 | CH$_3$ | iso-propyl | tert.-butyl | 68–79/0.1 | 70 |
| 9 | C$_2$H$_5$ | iso-propyl | tert.-butyl | 80–82/0.4 | 62 |
| 10 | C$_2$H$_5$ | CH$_3$ | sec.-butyl | 59–60/0.1 | 75.8 |
| 11 | C$_2$H$_5$ | CH$_3$ | iso-butyl | 61/.1 | 84 |
| 12 | C$_2$H$_5$ | C$_2$H$_5$ | iso-propyl | 55–56/0.02 | — |
| 13 | C$_2$H$_5$ | C$_2$H$_5$ | sec.-butyl | 56/0.02 | 81 |
| 14 | C$_2$H$_5$ | C$_3$H$_7$ | sec.-butyl | 59–60/0.02 | 80 |
| 15 | C$_2$H$_5$ | sec.-butyl | sec.-butyl | 67–69/0.05 | 74 |

EXAMPLE 13

Testing for Corn rootworm intrinsic activity, for corn phytotoxicity and activity against Southern Armyworm.

A. Corn rootworm intrinsic activity (CRW)

The test compound is prepared in a one percent solution with acetone or ethanol. The stock solution is then diluted with an aqueous solution of Tween 20 and water to the appropriate concentration (i.e., 100, 10, 1, 0.1, 0.05 ppm). Two ml of this solution is pipetted into a 9 cm. petri dish containing two layers of filter paper. Second instar larvae are introduced and the dish closed. Observations for mortality and moribund larvae are made after two days (48 hours) exposure. Insecticidal activity is primarily contact and vapor action with minimum ingestion. The results are tabulated in TABLE 1.

B. Corn phytotoxicity

Test compounds are dissolved in acetone to provide concentrations of 0.5 and 1.0% active ingredient. Corn seeds are planted in double rows in 9"×7" fiber flats containing pasteurized soil. Five seeds are planted in each furrow and lightly covered with soil. Treatment is made by applying 5 ml/row of test solution directly over the corn seed at the bottom of the furrow. The 0.5% and 1.0% solutions provide a rate of application equivalent to 1 and 2 lbs active ingredient/acre. After the furrows are closed, the flats are removed to the greenhouse, watered and held for observation and harvest. Three replicate flats are used for each treatment.

Assessment of corn tolerance after 11 days is made by rating the response of individual plants on a 0–10 scale (where 0=no effect and 10=complete kill). Overall ratings are made for each replicate flat 2 weeks after treatment. Assessment of corn tolerance is also based on fresh weight of shoots that are harvested after the two week visual rating. The results are tabulated in TABLE 2.

C. Southern Armyworm Intrinsic Activity (SAW)

Stock solution (1%) of test material was made in acetone and diluted to the desired concentration by a 500 ppm Tween 20 aqueous solution. Lima bean leaves are dipped into the solution and transferred to petri dishes (100×15 mm) containing two filter papers moistened with 2 ml water. Each petri dish contained one leaf and was kept open to dry out the solution on the leaf. Five third instar larvae of Southern Armworm (*Spodoptera eridania*) were added to the leaf and the dish was finally covered.

The insects were held at 78° F. for 72 hours and percent kill was recorded. The results are an average of two replicas.

TABLE 1

| | | % Kill | | | |
|---|---|---|---|---|---|
| Compound of | Rate (ppm) | CRW | | SAW | |
| Example | 1 | 0.1 | 0.05 | 500 | 100 |
| 2 | 100 | 100 | 55 | 100 | 65 |
| 3 | 100 | 100 | 100 | 100 | 100 |
| 4 | 100 | 100 | 85 | 100 | 100 |
| 5 | 100 | 85 | 65 | 100 | 95 |
| 6 | 100 | 90 | 60 | 100 | 10 |
| 7 | 95 | 50 | — | 60 | 0 |
| 10 | 100 | 100 | 100 | 90 | 10 |
| 11 | 95 | 55 | — | 60 | — |

TABLE 2

| | CORN PHYTOTOXICITY | | | |
|---|---|---|---|---|
| Compound | Percent Emergence | Rate lb/A | Rating By Plant | By Rep |
| Commercial | 53 | 1 | 6.2 | 6.0 |
|  | 57 | 2 | 6.9 | 6.7 |
| Example 2 | 87 | 1 | 0.7 | 2.0 |
|  | 87 | 2 | 0.9 | 2.3 |
| Untreated | 93 | — | 0 | 0 |

The commercial compound has the following structure:

$$\text{Ethyl O}-\overset{\overset{O}{\|}}{P}\begin{matrix}S-\text{n-propyl}\\ \\ S-\text{n-propyl}\end{matrix}$$

I claim:

1. A compound of the formula $$R-\overset{\overset{S}{\|}}{P}\begin{matrix}O-R_1\\ S-R_2\end{matrix}$$

in which
R is an alkyl of 1 to 8 carbon atoms;
$R_1$ is an alkyl of 1 to 8 carbon atoms; and
$R_2$ is alpha branched alkyl of 4 to 8 carbon atoms.

2. A compound of claim 1 in which $R_1$ is unbranched alkyl of 1 to 6 carbon atoms.

3. A compound of claim 1 in which $R_2$ is t-butyl.

4. A compound of claim 1 in which R is methyl or ethyl.

5. A compound of claim 1 in which
R is ethyl;
$R_1$ is ethyl; and
$R_2$ is t-butyl.

6. A compound of claim 1 in which
R is ethyl;
$R_1$ is methyl; and
$R_2$ is t-butyl.

7. A compound of claim 1 in which
R is methyl;
$R_1$ is methyl; and
$R_2$ is t-butyl.

8. A compound of claim 1 in which
R is methyl;
$R_1$ is ethyl; and
$R_2$ is t-butyl.

9. A compound of claim 1 in which
R is methyl;
$R_1$ is n-propyl; and
$R_2$ is t-butyl.

10. A compound of claim 1 in which $R_2$ is tertiary alkyl.

11. A method for controlling insects and nematodes which comprises applying thereto a pesticidal amount of a compound of the formula $$R-\overset{\overset{S}{\|}}{P}\begin{matrix}O-R_1\\ S-R_2\end{matrix}$$

in which
R is an alkyl of 1 to 8 carbon atoms;
$R_1$ is an alkyl of 1 to 8 carbon atoms; and
$R_2$ is alpha branched alkyl of 4 to 8 carbon atoms.

12. A method for controlling corn rootworm which comprises providing a pesticidal amount in the soil of a compound of the formula $$R-\overset{\overset{S}{\|}}{P}\begin{matrix}O-R_1\\ S-R_2\end{matrix}$$

in which
R is an alkyl of 1 to 8 carbon atoms;
$R_1$ is an alkyl of 1 to 8 carbon atoms; and
$R_2$ is alpha branched alkyl of 4 to 8 carbon atoms.

13. The method of claim 12 in which $R_1$ is unbranched alkyl of 1 to 6 carbon atoms.

14. The method of claim 12 in which $R_2$ is t-butyl.

15. The method of claim 12 in which R is methyl or ethyl.

16. The method of claim 12 in which R is methyl or ethyl;
$R_1$ is unbranched; and
$R_2$ is branched on the carbon atom bonded to S.

17. The method of claim 12 in which
R is ethyl;
$R_1$ is ethyl; and
$R_2$ is t-butyl.

18. The method of claim 12 in which
R is ethyl;
$R_1$ is methyl; and
$R_2$ is t-butyl.

19. The method of claim 12 in which
R is methyl;
$R_1$ is methyl; and
$R_2$ is t-butyl.

20. The method of claim 12 in which
R is methyl;
$R_1$ is n-propyl; and
$R_2$ is t-butyl.

21. The method of claim 12 in which
R is ethyl;
$R_1$ is n-propyl; and
$R_2$ is t-butyl.

22. The method of claim 11 in which $R_2$ is tertiary alkyl.

23. The method of claim 12 in which $R_2$ is tertiary alkyl.

24. A composition for controlling insects or nematodes comprising as the active ingredient a compound of the formula $$R-\overset{\overset{S}{\|}}{P}\begin{matrix}O-R_1\\ S-R_2\end{matrix}$$

in which
R is an alkyl of 1 to 8 carbon atoms;
$R_1$ is an alkyl of 1 to 8 carbon atoms; and
$R_2$ is alpha branched alkyl of 4 to 8 carbon atoms;
and an inert, non-phytotoxic organic solvent or a solid carrier; said active ingredient being present in an amount effective as an insecticide or a nematocide.

25. The composition of claim 24 in which $R_2$ is tertiary alkyl.

26. The composition of claim 24 in which $R_2$ is t-butyl.

* * * * *